(12) United States Patent
Young et al.

(10) Patent No.: US 8,614,179 B2
(45) Date of Patent: Dec. 24, 2013

(54) ANTIBACTERIAL COMBINATION THERAPY FOR THE TREATMENT OF GRAM POSITIVE BACTERIAL INFECTIONS

(75) Inventors: Malcolm Philip Young, Hexham (GB); Catherine Mary Thomas, Sutton Coldfield (GB)

(73) Assignee: E-Therapeutics PLC, Newcastle Upon Tyne (GB)

( * ) Notice: Subject to any disclaimer, the term of this patent is extended or adjusted under 35 U.S.C. 154(b) by 33 days.

(21) Appl. No.: 13/054,491

(22) PCT Filed: Jul. 17, 2009

(86) PCT No.: PCT/GB2009/001772
§ 371 (c)(1),
(2), (4) Date: Jul. 8, 2011

(87) PCT Pub. No.: WO2010/007381
PCT Pub. Date: Jan. 21, 2010

(65) Prior Publication Data
US 2011/0257078 A1    Oct. 20, 2011

(30) Foreign Application Priority Data
Jul. 18, 2008 (GB) .................................. 0813211.0

(51) Int. Cl.
*A01N 37/18* (2006.01)
*A61K 38/04* (2006.01)

(52) U.S. Cl.
USPC ............... 514/2.7; 514/2.9; 514/99; 514/380; 514/2.8

(58) Field of Classification Search
None
See application file for complete search history.

(56) References Cited

U.S. PATENT DOCUMENTS

| 3,249,109 | A | 5/1966 | Maeth et al. |
| 3,598,122 | A | 8/1971 | Zaffaroni |
| 4,144,317 | A | 3/1979 | Higuchi et al. |
| 4,262,003 | A | 4/1981 | Urquhart et al. |
| 4,307,717 | A | 12/1981 | Hymes et al. |
| 4,911,932 | A | 3/1990 | Clum et al. |
| 7,485,294 | B2 | 2/2009 | Bourgeois et al. |
| 2010/0144626 | A1 | 6/2010 | Young et al. |
| 2011/0039906 | A1 | 2/2011 | Young et al. |
| 2011/0257078 | A1 | 10/2011 | Young et al. |

FOREIGN PATENT DOCUMENTS

| EP | 0666077 A1 | 8/1995 |
| GB | 2185187 A | 7/1987 |
| GB | 2216796 A * | 10/1989 |
| WO | 0010582 A2 | 3/2000 |
| WO | 2005096990 A2 | 10/2005 |
| WO | 2008059258 A2 | 5/2008 |
| WO | WO 2008059258 A2 * | 5/2008 |
| WO | 2009013480 A2 | 1/2009 |
| WO | 2009037264 A2 | 3/2009 |
| WO | WO 2009081117 A1 * | 7/2009 |

OTHER PUBLICATIONS

Cornelissen and Van den Bossche "Synergism of the Antimicrobial Agents Miconazole, Bacitracin and Polymixin B" Chemotherapy 29:419-427. Published 1983.*
Giacometti et al "Combination studies between polycationic peptides and clinically used antibiotics against Gram-postive and Gram-negative bacteria" Peptides 21:1155-1160. Published 2000.*
Moellering et al "Species-Specific Resistance to Antimicrobial Synergism in *Streptococcus faecium* and *Streptococcus faecalis*" J Infect Dis 140:203-208. Abstract only. Published 1979.*
Kerr et al "Activity of nisin against *Clostridium difficile*" The Lancet 349:1025-1026. Published Apr. 5, 1997.*
Written Opinion of PCT International Search Report for International Application No. PCT/GB2009/001772, mailed Oct. 19, 2009 (7 pages).
Cornelissen et al., "Synergism of the Antimicrobial Agents Miconazole, Bacitracin and Polymyxin B" Chemotherapy, S. Krager, Basel, CH, vol. 29, No. 6, pp. 419-427 (1983).
Moneib, "In-Vitro Activity of Commonly Used Antifungal Agents in the Presence of Rifampin, Polymyxin B and Norfloxacin against *Candida albicans*." Journal of Chemotherapy, vol. 7, No. 6, pp. 525-529 (1995).
Studdert et al., "A clinical trial of a topical preparation of miconazole, polymyxin and prednisolone in the treatment of otitis externa in dogs." Australian Veterinary Journal, 1991, vol. 68, No. 6, pp. 193-195 (1991).
Burdon et al., "Antibiotic susceptibility of *Clostridium difficile*." The Journal of Antimicrobial Chemotherapy, vol. 5, No. 3, pp. 307-310 (1979).
Angeles et al., "Peptide antibiotic and actin-binding protein as mixed-type inhibitors of *Clostridium difficile*CDT toxin activities." Biochemical and Biophysical Research Communications, Academic Press, Inc., vol. 327, No. 1, pp. 361-370 (2005).
Ugurlu et al., "Colonic delivery of compression coated nisin tablets using pectin/HPMC polymer mixture" European Journal of Pharmaceutics and Biopharmaceutics, Elsevier Science Publishers B.V., vol. 67, No. 1, pp. 202-210 (2007).

(Continued)

*Primary Examiner* — Cecilia J Tsang
*Assistant Examiner* — Zachary J. Miknis
(74) *Attorney, Agent, or Firm* — K&L Gates LLP (57) ABSTRACT

There is described a composition comprising a therapeutically active imidazole, and derivatives thereof, and an agent active on a bacterial cell surface selected from the group consisting of one or more of colistin, nisin, D-cycloserine, fosfomycin, fosfomycin trometamol, fosfomycin disodium and polymixin B, and derivatives thereof.

4 Claims, 3 Drawing Sheets

(56) References Cited

OTHER PUBLICATIONS

Database Biosis [On line] Biosciences Information Service, Philadelphia, PA, US; Jan. 2001, Nikolaeva I V et al., "Drug resistance of *Staphylococcus aureus* strains isolated form children with intestinal dysbacteriosis." Database accession No. PREV200100522062.

Cunha B, "New Uses for Older Antibiotics: Nitrofurantoin, Amikacin, Colistin, Polymyxin B, Doxycycline, and Minocycline Revisited", Medical Clinics N. Am, vol. 90, No. 6, pp. 1089-1107 (2006).

Pietschmann et al., "Synergistic effects of Micanzole and Polymyxin B on Microbial Pathogens", Veterinary Research Communications, vol. 33, No. 6, pp. 489-505 (2009).

Lee et al., "Antibacterial Activity of Antimycotic Miconazole against Methicillin-Resistant *Staphylococcus aureus*," J. Microbiol. Biotechnol., vol. 9, No. 5, pp. 572-575 (1999).

Khalil et al., "Comparative Activity of Clotrimazole, Miconazole, Ketoconazole and Pharmaceutical Preparations against Multiresistant *Staphylococcus aureus*Isolates," Alexandria Journal of Pharmaceutical Sciences, vol. 13, No. 2, pp. 97-100 (1999).

Yoshida et al., "Treatment of Severe Pneumonia due to Methicillin-Resistant *Staphylococcus aureus* (MRSA) and *Candida krusei* with Granulocyte Colony-Stimulating Factor (G-CSF): a Case Report," Kansenshogaku zasshi., The Journal of the Japanese Association for Infectious Diseases, vol. 67, No. 8, pp. 767-771, Abstract (1993).

Antolini et al., "Analogues of 4,5-bis(3,5-Dichlorophenyl)-2-Trifluoromethyl-1H-Imidazole as Potential Antibacterial Agents," Bioorganic & Medicinal Chemistry Letters, 9(7):1023-1028, (1999).

Cartwright, "Clotrimazole in the Treatment of Acute and 'Resistant' Vaginal Candidiasis," Postgraduate Medical J., 50(1 SUP): pp. 90-92, (1974).

Miura et al., "Anti-MRSA Activity of 1-(4-Chlorophenyl)-3-Dichlorophenyl- and 3-Trichlorophenyl-2-(1H-Imidazol-1-YL)-2-Propen-1-One Derivatives," J. of Antibiotics, 47(10): pp. 1171-1172, (1994).

Stevens, "Susceptibility of Candida Species to Clotrimazole (CZ) in the Era of Increasing Fluconazole (FZ) Resistance," Abstracts of the General Meeting of the American Society for Microbiology, 99(2):321, (Jun. 2, 1999).

Taylor et al., "In vitro Antimicrobial Activity of Diethyldithiocarbamate and Dimethyldithiocqarbamate Against Methicillin-resistant *Staphylococcus*," Annals of Clinical and Laboratory Science, vol. 17, No. 3, pp. 171-177, (1987).

Borisy et al., "Systematic discovery of multicomponent therapeutics," Proceedings of the National Academy of Sciences of USA, 100(13), pp. 7977-7982, (Jun. 24, 2003).

Phillips et al., "Disulfiram Inhibits the In Vitro Growth of Methicillin-Resistant *Staphylococcus aureus*," Antimicrobial Agents and Chemotherapy, 35(4): pp. 785-787, (1991).

Sauna et al., "Disulfiram, an old drug With new potential therapeutic uses for human cancers and fungal infections," Molecular BioSystems, 1(2): pp. 127-134, (2005).

Shukla et al., "Disulfiram is a potent modulator of multidrug transporter Cdr1p of *Candida albicans*," Biochemical and Biophysical Research Communications, 322(2): pp. 520-525, (2004).

Wang-sheng et al. "In Vitro antibacterial activity of econazole nitrate against staphylococci," Chinese J. of Antibiotics, 29(11): pp. 684-686, (2004).

\* cited by examiner

United States Patent US 8,614,179 B2

ANTIBACTERIAL COMBINATION THERAPY FOR THE TREATMENT OF GRAM POSITIVE BACTERIAL INFECTIONS

FIELD OF THE INVENTION

The present invention provides a product comprising a synergistic combination of a therapeutically active imidazole and a bacterial cell membrane or cell wall active agent, or a derivative or a metabolite thereof, as a combined preparation for the treatment of infections caused or contributed to by gram-positive bacteria.

BACKGROUND

Gram-positive bacteria, such as *Staphylococci*, *Enterococci* and *Clostridia*, are extremely important, pathogens in both human and veterinary medicine. In the United States, between 1995 and 1998, 60% of hospital bloodstream infections involved gram-positive bacteria. This percentage is continuing to increase. The development of antibiotic resistance amongst gram-positive bacteria complicates treatment and can lead to increased morbidity and mortality.

Antibiotic resistance in bacteria has been selected through the prolific use of these drugs both in human medicine and animal husbandry, indiscriminate prescribing practices, and patient non-compliance with treatment regimes. Therapeutic options for the treatment of such drug-resistant microorganisms, especially gram-positive bacteria, are becoming increasingly limited. The problem of antibiotic resistance is exacerbated by the spread of drug-resistant organisms, and the dissemination of resistance genes between bacteria. The threat to the successful management of bacterial infections posed by the development and spread of antibiotic resistance is one of the most significant problems within healthcare and veterinary medicine.

Staphylococci

*Staphylococci* are major causes of serious healthcare associated infection (HAI). Of particular note are strains of *Staphylococcus* that have developed or obtained varying levels of resistance to antibiotics such as methicillin (meticillin). These difficult-to-treat organisms are commonly known as methicillin resistant *Staphylococcus aureus* (MRSA) and methicillin resistant *Staphylococcus epidermidis* (MRSE). Approximately 80% of *S. epidermidis* isolates from device-associated infections are methicillin resistant (MRSE) as well as being multi-resistant. Resistance to multiple antibiotics and the ability of *S. epidermidis* to form biofilms on inert surfaces exacerbate the challenges of treating infections caused by these organisms.

In the USA, over 50% of clinical *S. aureus* isolates are resistant to the β-lactam methicillin (NNIS, 2004). Similarly, reports of methicillin-resistant *S. aureus* (MRSA) in animals have become more frequent in recent years (O'Mahony et al., 2005); MRSA has been isolated from dogs, cats, cattle, sheep, chickens, rabbits and horses (Devriese and Hommez, 1975, Hartmann et al., 1997, Pak et al., 1999, Tomlin et al., 1999, Lee, 2003, Goni et al., 2004, and Weese 2004).

In both human and veterinary medicine, bacterial biofilms (structured communities of bacterial cells enclosed in a self-produced polymeric matrix and adherent to an inert or living surface (Costerton et al., 1999)) are a significant problem. In animal husbandry, bacterial biofilms can develop on poultry processing instrumentation (Arnold & Silvers, 2000) and may cause treatment failure of mastitis in cows infected with *S. aureus* (Melchior et al., 2006). In human healthcare, biofilms of bacteria have been shown to colonise many medical devices, including orthopaedic implants (Bahna et al., 2007). In the UK, 35% of hip prostheses' infection is attributable to *S. aureus*, resulting in septic loosening, fracture non-union and osteomyelitis (Sanderson, 1991). The association of MRSA with the use of orthopaedic devices is extremely problematic due to the increased spectrum of resistance of this organism, in addition to the protection from the immune system given by the biofilm growth phase, often necessitating the removal of a contaminated device, causing further trauma to the patient and increasing medical costs. Colonisation with MRSA is the general precursor to the development of an MRSA infection, so interventions that reduce levels of human colonisation or the colonisation of surfaces such as medical devices will reduce the spread of infections in healthcare facilities.

The acquisition of methicillin resistance among *Staphylococcal* species not only precludes the use of all currently available β-lactam antibiotics, but also is commonly associated with resistance to multiple drug classes.

Methicillin resistance in *Staphylcocci* develops by the alteration of the target of the drug. β-lactam antibiotics, such as methicillin, act on sensitive strains by binding to and inhibiting proteins called "Penicillin Binding Proteins". Resistance to methicillin in *Staphylococci* occurs by the alteration one of these proteins, PBP2', so that β-lactams bind poorly to it. This results in the bacterium becoming resistant to all currently available β-lactam drugs. MRSA and MRSE infections can be treated with glycopeptide drugs, such as vancomycin. The rise in prevalence of MRSA and MRSE, in addition to emerging high levels of resistance to aminoglycosides and ampicillin in *Enterococci*, have resulted in an increased reliance on vancomycin. This has driven the subsequent emergence of vancomycin resistant pathogens. Of particular note are strains commonly known as vancomycin intermediately sensitive *Staphylococcus aureus* (VISA) and vancomycin resistant *Staphylococcus aureus* (VRSA), all of which are multi-drug resistant and difficult to treat. The emergence of VISA and VRSA means that current antibiotics may become ineffective for the treatment of human infections such as endocarditis, bacteraemia and osteomyelitis.

The administration of vancomycin to patients with recurrent MRSA infections causes an increased risk of the emergence of VISA or VRSA strains. The vast majority of VISA infections in the USA occur in patients with recurrent MRSA treated with vancomycin (Appelbaum, 2006). Although a dramatic reduction in the use of glycopeptides such as vancomycin would reduce the emergence and spread of VISA and VRSA, this is not practical without the use of alternative compounds that do not promote the emergence of multiple resistance.

Clostridia

*Clostridia* are multi-drug resistant Gram-positive bacteria that are becoming one of the most difficult to treat healthcare-associated infections to date. The administration of broad-spectrum antibiotics, such as ampicillin, amoxicillin and the cephalosporins, plays a key role in the development of *Clostridium difficile*-associated diarrhoea (CDAD). The presence of a large number of mobile genetic elements within the genome of *C. difficile* are thought to be responsible for the multiple-drug resistance observed in this species. The use of broad-spectrum antibiotics reduces bacterial colonisation in the intestine, permitting the overgrowth of *C. difficile*. *Clostridium difficile* is extremely hardy; by forming spores, it can survive extremes of temperature, ethanol and antibiotics, and so is very difficult to treat. One of the key challenges in the treatment of *C. difficile* is the fact that it is able to form these highly resistant spores. As such, antibiotic treatment commonly results in the inhibition of the actively growing *Clostridium* cells but not the vegetative spores. The spores remain in the gut of a mammal after treatment and can then germinate resulting in a new *C. difficile* infection. Currently the antibiotics of choice for the treatment of *C. difficile* are metronidazole and then vancomycin if metronidazole is ineffective. However, neither of these drugs is able to inhibit the outgrowth of *Clostridium* spores, and as such the prevalence of relapses in *C. difficile* infection after treatment is estimated at around 55% of all cases.

Initially, oral vancomycin was used as a primary drug choice in the treatment of CDAD, but because of the risk of promotion and selection of vancomycin resistant gut flora (such as *Enterococci*), vancomycin is recommended only for cases that do not respond to the primary treatment (metronidazole). Recently, resistance to vancomycin and metronidazole in *C. difficile* isolates has been reported, and the use of these agents has been shown to increase the density of vancomycin-resistant *Enterococcus* (VRE) in the stools of colonised patients.

In summary, there are three key factors to be considered when designing novel therapeutics agents for the treatment of *Clostridia*, these are:
1. The drug must be able to kill the multiply-resistant actively growing *Clostridia* to give efficient relief to the patient from the disease.
2. The drug must be able to prevent the outgrowth of *Clostridium* spores to minimise the likelihood of a relapse.
3. A drug that does not promote the spread of vancomycin resistance is preferable.

Enterococci

The development of vancomycin-resistant *Enterococci* (VRE) in recent years is of major significance. *Enterococci* once were viewed as harmless inhabitants of the human and animal gut flora, but have now acquired resistance to multiple classes of antibiotic, including the last-resort drug, vancomycin. In the US, the prevalence of *Enterococcus faecium* exhibiting vancomycin resistance rose from 26.2% in 1995 to around 70% in 2004, making it one of the most feared pathogens in US hospitals.

The acquisition of vancomycin resistance among some strains of *Enterococci* is associated with resistance to multiple drug classes due to the sequential nature at which these strains have acquired resistance to every new antibiotic challenge.

Genotypes and Phenotypes of Multi-Drug Resistant Gram Positives

MRSA, MRSE, VISA, VRSA and VRE are genotypically and phenotypically distinct from other, sensitive *Staphylococci* and *Enterococci*, tending to form discrete clonal lineages.

The most prevalent clones of MRSA in the UK are EMRSA-15 and EMRSA-16; EMRSA-16 is regarded as endemic in the majority of UK hospitals. These MRSA clones differ from other *Staphylococci* by the presence of a cassette of several genes (the SCCmec gene cassette), and are commonly resistant to many different classes of antibiotic in addition to methicillin. This gene cassette contains the genes for methicillin resistance as well as genes important for enabling the cassette to move between strains; it commonly contains many other genes encoding resistance to other antibiotic classes. A genetic comparison between an EMRSA-16 strain and a sensitive *Staphylococcal* strain revealed that the MRSA strain contained an extra 106 genes, many of which were important for the virulence and drug resistance of the strain.

Similarly, VRE and *Clostridium* outbreaks are commonly clonal, with the vanA gene cassette (coding for cell-wall precursors that do not bind to vancomycin) being the most prevalent genetic resistance mechanism in VRE outbreaks. In the UK it is estimated that only 3 clonal strains of *C. difficile* are responsible for around 75% of all CDAD cases.

Mechanisms of Drug Resistance

Drug resistance can be specific, i.e. particular to a certain drug or class of drugs, or non-specific in that the resistance applies to a range of drugs, not necessarily related. In the case of VISA, an increase in cell wall thickness is a major contributor to the observed drug resistance.

VISA and VRSA may be defined as any *Staphylococcal* strain with a vancomycin MIC of 4-8 mg/L (VISA) or greater or equal to 8 mg/L (VRSA). These levels of resistance can be due to an increase in cell wall thickness, by the production of cell-wall precursors incapable of binding vancomycin, or via another mechanism. Susceptible gram-positive organisms synthesise cell wall precursors ending in D-ala-D-ala, whereas vancomycin resistant gram-positive organisms, such as VISA, VRSA and VRE synthesise, for example, D-ala-D-lac precursors. The presence of vancomycin resistance in *Staphylococcal* and *Enterococcal* strains may be identified by the measurement of the MIC to vancomycin by broth or agar dilution, or by Etest®, or by the identification of vanA, vanB, vanC, vanD, vanE, vanG genes, or similar, by polymerase chain reaction (PCR). The current invention also encompasses the subclass of VISA strains that are heterogeneous VISA (hVISA); these are vancomycin susceptible methicillin-resistant *Staphylococcus aureus* by conventional testing but have a sub-population of intermediately resistant cells. hVISA strains are thought to be the precursors of VISA.

Management of Multi-Drug Resistant Gram Positive Infections

The management of human infections caused by MRSA, MRSE, VISA, VRSA and VRE reflect the genotypic and phenotypic differences outlined above, and require greater investment in hospital infrastructure, facilities for patient isolation, and infection control measures than for other strains of *Staphylococci* and *Enterococci*. The ease at which *Clostridium difficile* can spread within the hospital environment, and the ability of the bacterium to form highly-resistant spores, means that *C. difficile* infections also require more extensive infection control measures than those required for most other gram-positive infections; recent cost estimates attributable to CDAD in the UK and USA exceed US$4,000 per case.

The treatment options for infections contributed to or caused by VISA, VRSA and VRE are now severely limited. Resistance against the two newest antibiotics for VRE (quinupristin-dalfopristin and linezolid) as been described; linezolid has already been associated with treatment failure in VRE infections. There is an urgent need to discover new compounds that inhibit or kill such organisms, and to limit the development and spread of these multiply-resistant pathogens.

Current treatment for *Clostridium difficile* is not always effective; there are increasing reports of recurring infection and resistance development. CDAD recurs after treatment in up to 55% of patients. Because of the limited therapeutic options for the treatment of CDAD and the high recurrence rate, new therapeutic strategies targeting both the growing bacterial cells and vegetative spores are urgently needed.

It has been found that certain imidazoles and or their derivatives are capable of inhibiting the growth of *Clostridium difficile* (George, 1979), MRSA (Lee & Kim, 1999) and/or VISA, VRSA and VRE. However, the identification of compounds that act synergistically with these drugs (the imidazoles) means that lower concentrations of original drug may be used (thus reducing the undesirable side effects of the imidazoles) and prolonging the life of the drug treatment (e.g. a synergistic combination of two drugs will require resistance to develop in both components before the combination becomes ineffective). If the spontaneous rate of resistance development in an organism is $10^8$, the development of resistance to the combination of two compounds will be approximately $10^6$, therefore the risk of resistance developing is dramatically lower.

Synergy between antibiotics may occur when two antibiotics target bacterial proteins within the same metabolic pathway. Trimethoprim and sulphamethoxazole are commonly administered together as co-trimoxazole because they target two different enzymes in the bacterial folic acid synthesis pathway. Synergy may also occur when a resistance mechanism, such as an efflux pump, is inhibited, permitting the accumulation of an antibiotic that if administered singly, may be removed by the efflux pump. There is no known technique by which to predict that two compounds will act synergistically to give an antibacterial effect greater than the sum of the effects of the individual drugs, unless the mechanism of action of each agent is known, and even then, synergy is not guaranteed. Similarly, if a compound acts synergistically with a particular antibiotic, it cannot be predicted that a combination with an antibiotic acting on different bacterial targets or on different bacterial strains will also exhibit synergy.

It is known that bacitracin and miconazole act synergistically against *Staphylococcus aureus* and *Staphylococcus epidermidis* (Cornelissen and Bossche, 1983). However, when this combination was tested against multi-drug resistant strains such as MRSA and VISA (this specification, Table 3), synergy did not occur. This highlights the fact that phenotypic and genotypic differences between sensitive and resistant strains prevents the prediction of synergy from data generated on sensitive strains. Additionally, not all cell wall or membrane active agents will demonstrate synergy with miconazole or other imidazoles when used to kill or inhibit the growth of bacteria.

Nisin is known to have in vitro activity against *C. difficile* (Bartoloni A et al, 2004; Kerr et al, 1997) and the potential for nisin and vancomycin to be synergistic is disclosed. However, as described above, this information does not allow predictions of synergy of nisin with other antibiotics, especially as there is a lack of clarity over the exact mode of action of miconazole against *Clostridium*. For example, nisin does not act synergistically with other antibiotics such as bacitracin and chloramphenicol, which like vancomycin also act on the cell wall (chloramphenicol causes an accumulation of cell wall peptidoglycan). Indeed, nisin was found to antagonise the antibacterial activity of chloramphenicol, thus, one cannot predict that synergy will occur with nisin and miconazole.

Similarly, fosfomycin, and derivatives thereof, is known to be active against some sensitive Gram positive bacteria, and synergy has been shown with some antibiotics (such as rifampicin and linezolid) but not with other antibiotics (e.g. vancomycin) (Grif et al, 2001). This demonstrates that the detection of synergy with some antibiotics cannot be used to generate blanket predictions of synergy with other drugs.

The present invention discloses the knowledge that the combination of certain imidazoles with one or more specific agents active on a bacterial cell membrane or bacterial cell wall, is capable of inhibiting the growth of MRSA, MRSE, VISA, VRSA, VRE and *Clostridia* at dramatically lower concentrations than either agent used singly, or their additive effect. The combination of miconazole with nisin demonstrates surprising synergy against the actively growing cells, but an additional benefit of this combination is that the nisin component also acts on the vegetative cells by inhibiting their outgrowth, thus reducing the likelihood of a relapse in infection.

An objective of the present invention is to provide a new and effective treatment for infections contributed to or caused by difficult to treat gram-positive bacteria, such as, MRSA, MRSE, VISA, VRSA, VRE and *Clostridia*.

SUMMARY OF THE INVENTION

In a first aspect, the present invention provides a composition comprising a therapeutically active imidazole, and derivatives thereof, and an agent active on a bacterial cell surface selected from the group consisting of one or more of colistin, nisin, D-cycloserine, fosfomycin, and polymixin B, and derivatives thereof.

A bacterial cell has an internal structure (comprising DNA, ribosomes, storage granules and sometimes endospores) and a surface structure (comprising a cell wall and a cell membrane, and in some bacteria, a capsule, outer membrane and periplasmic space). Thus, the term "an agent active on a bacterial cell surface" used herein, refers to an agent that exerts its effects on the bacterial cell by acting on one or more bacterial cell surface components, such as the cell wall or the cell membrane, etc.

These agents, and derivatives thereof, are advantageous, inter alia, in the following ways, nisin forms pores in the bacterial cell membrane; colistin and/or polymixin B disrupt the bacterial cell membrane, e.g. through a detergent like mechanism; D-cycloserine interferes with an early step in bacterial cell wall synthesis in the cytoplasm by competitive inhibition of two enzymes; and fosfomycin prevents the formation of N-acetylmuramic acid, an essential element of the peptidoglycan cell wall of bacteria.

Exemplary compounds comprising a therapeutically effective imidazole for use in connection with the present invention are provided by the following general formula (Formula I):

Formula I wherein $R_1$ and $R_2$ are independently selected from hydrogen lower alkyl, phenyl or substituted phenyl, wherein said substituted phenyl contains at least one phenyl substituent selected from the group consisting of halo, lower alkyl and lower alkoxy;

R is independently selected from hydrogen, lower alkyl, phenyl or substituted phenyl wherein said substituted phenyl contains at least one phenyl substituent selected from the group consisting of halo, lower alkyl and lower alkoxy;

$n_1$ is zero or 1;

X is oxy, S, NH or O;

$n_2$ is zero or 1;

$n_3$ is zero, 1 or 2

X' is S, Oxy or not present

Ar is independently selected from the group consisting of phenyl, substituted phenyl, thienyl and halothienyl, said substituted phenyl containing at least one phenyl substituent selected from the group consisting of halo, lower alkyl and lower alkoxy; $n_4$ is zero or 1

Ar' is a member selected from the group consisting of phenyl, substituted phenyl and α-tetralyl, said substituted phenyl containing at least one phenyl substituent selected from the group consisting of phenyl, thienyl, phenyl thio, halo, lower alkyl, lower alkoxy, cyano, nitro and amino;

R' is a member selected from the group consisting of hydrogen, methyl and ethyl; and R" is a member selected from the group consisting of hydrogen and methyl;

provided that:
  (i) when X is NH, then said R is hydrogen;
  (ii) when said Ar' is a substituted phenyl containing at least one phenyl substituent selected from the group consisting of nitro and amino, then said X is oxy and said $n_3$ is zero;
  (iii) when said Ar' is α-tetralyl, then said X is NH and said $n_3$ is zero; and
  (iv) when X is oxy and said Ar' is a member selected from the group consisting of phenyl and substituted phenyl containing at least one phenyl substituent selected from the group consisting of halo, lower alkyl, lower alkoxy and cyano, then said $n_3$ is other than zero;

and derivatives thereof.

It is to be understood that the terms "lower alkyl" and "lower alkoxy" encompass straight or branch chained hydrocarbons having from about 1 to about 6 carbons, such as, for example, methyl, ethyl, propyl, isopropyl, butyl, pentyl, hexyl and the like alkyls, and, respectively, the corresponding alkoxy such as methoxy, ethoxy, propoxy, isopropoxy, etc.

The preferred lower alkyl and lower alkoxy are methyl and methoxy, respectively. Furthermore, the term "halo" refers to halogens of atomic weight less than 127, i.e., fluoro, iodo, bromo and chloro. Preferred substituted phenyls with respect to the symbol Ar are mono-, di- and trihalo-phenyl, thiol-dihalo-phenyl, lower alkylphenyl and lower alkoxy phenyl; and mono-, di- and tri-halophenyl, di-phenyl, thiol-phenyl, lower alkoxyphenyl, cyanophenyl, mono-, di-nitrophenyl and amino phenyl with regard to the symbol Ar'.

Of particular interest are the therapeutically active imidazoles selected from the group consisting of clotrimazole, econazole, miconazole, butoconazole, fenticonazole, oxiconazole nitrate, sertaconazole, and sulconazole, and derivatives thereof.

Especially of interest are the therapeutically active imidazoles selected from the group 1-[(2-Chlorophenyl)diphenylmethyl]-1H-imidazole ($C_{22}H_{17}ClN_2$), clotrimazole; 1-[2-[(4-Cholorphenyl)methoxy]-2-(2,4-dichlorophenyl)ethyl]-1H-imidazole ($C_{18}H_{15}Cl_3N_2O$), econazole; and 1-[2-(2,4-Dichlorophenyl)-2-[(2,4-dichlorophenyl)methoxy]ethyl]-1H-imidazole ($C_{18}H_{14}Cl_4N_2O$), miconazole; and derivatives thereof.

The formulae for each of these compounds are as follows:

Clotrimazole

Econazole

Miconazole

Other imidazole compounds of interest include (±)-1-[4-(4-Chlorophenyl)-2-[(2,6-dichlorophenyl)thio]butyl]-1H-imidazole ($C_{19}H_{17}Cl_3N_2S$: Butoconazole), 1-[2-(2,4-Dichlorophenyl)-2-[[4-phenylthio)phenyl]methoxy]ethyl]-1H-imidazole ($C_{24}H_{20}Cl_2N_2OS$: Fenticonazole), (Z)-1-(2,4-Dichlorophenyl)-2-(1H-imidazol-1-yl)ethanone O-[2,4-dichlorophenyl)-methyl]oxime mononitrate ($C_{18}H_{14}Cl_4N_4O_4$: Oxiconazole Nitrate), 1-[2-[(7-chlorobenzothiophen-3-yl)methoxy]-2-(2,4-dichlorophenyl)-ethyl] imidazole ($C_{20}H_{15}Cl_3N_2OS$: Sertaconazole), and 1-[2-[[(4-chlorophenyl)methyl]-thio]-2-(2,4-dichlorophenyl)ethyl]-1H-imidazole ($C_{18}H_{15}Cl_3N_2S$: Sulconazole); and derivatives thereof.

The term "derivative" shall include, but shall not be limited to, metabolites, pro-drugs and/or a pharmaceutically acceptable salt. The term "pharmaceutically acceptable salt" refers to salts that retain the biological effectiveness and properties of the compounds described herein and, which are not biologically or otherwise undesirable. Pharmaceutically acceptable acid addition salts can be formed with inorganic acids and organic acids, e.g., acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Inorganic acids from which salts can be derived include, for example, hydrochloric acid, hydrobromic acid, sulphuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Pharmaceutically acceptable base addition salts can be formed with inorganic and organic bases. Inorganic bases from which salts can be derived include, for example, sodium, disodium, potassium, lithium, ammonium, calcium, magnesium, iron, zinc, copper, manganese, aluminium, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, ethanolamine and trometamol (tromethamine). The pharmaceutically acceptable salts of the present invention can be synthesized from a parent compound, a basic or acidic moiety, by conventional chemical methods. Such salts may be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid.

Thus, preferred salts of the imidazoles are generally the nitrates. Therefore, the invention in particular provides, for example, an imidazole nitrate, such as, miconazole nitrate ($C_{18}H_{14}Cl_4N_2O \cdot HNO_3$), and econazole nitrate ($C_{18}H_{15}Cl_3N_2O \cdot HNO_3$). Preferred salts of the fosfomycin are, for example, the disodium salt and the trometamol salt.

In a further preferred embodiment, the present invention provides a composition comprising one or more of clotrimazole, clotrimazole nitrate, econazole, econazole nitrate, miconazole, miconazole nitrate in combination with one or more of colistin, nisin, D-cycloserine, fosfomycin, and polymixin B, and derivatives thereof.

Accordingly, and in one embodiment, the present invention provides a composition comprising one or more of clotrimazole, clotrimazole nitrate, econazole, econazole nitrate, miconazole, miconazole nitrate in combination with an agent active on a bacterial cell surface selected from the group consisting of one or more of colistin, nisin, D-cycloserine, fosfomycin, and polymixin B, and derivatives thereof, for the treatment of an infection contributed to or caused by gram-positive bacteria, such as, MRSA, MRSE, VISA, VRSA, VRE and/or *Clostridia* spp.

In a further preferred embodiment, the present invention provides a composition comprising one or more of clotrimazole, clotrimazole nitrate, econazole, econazole nitrate, miconazole, miconazole nitrate in combination with one or more of colistin, nisin, D-cycloserine, fosfomycin, and polymixin B, and derivatives thereof.

Thus, according to one particular aspect of the invention we provide a composition comprising miconazole, and derivatives thereof, and fosfomycin, and derivatives thereof. The composition according to this aspect of the invention is especially suitable for the treatment of multi-drug resistant bacterial infections in adults, e.g. for intravenous administration.

According to another particular aspect of the invention we provide a composition comprising miconazole, and derivatives thereof, and nisin, and derivatives thereof. The composition according to this aspect of the invention is especially suitable for the treatment of infections contributed to or caused by the multi-drug resistant Gram positive organisms of the *Clostridium* genus, It may be convenient or desirable to prepare, purify, and/or handle a corresponding solvate of the compounds described herein, which may be used in any one of the uses/methods described. The term solvate is used herein to refer to a complex of solute, such as a compound or salt of the compound, and a solvent. If the solvent is water, the solvate may be termed a hydrate, for example a mono-hydrate, di-hydrate, tri-hydrate etc, depending on the number of water molecules present per molecule of substrate.

In particular, the present invention provides a composition as hereinbefore described for treating an infection contributed to or caused by gram-positive bacteria.

The present invention provides a composition as hereinbefore described for treating an infection contributed to or caused by a difficult to treat gram-positive bacterium.

Difficult to treat bacteria include, but shall not be limited to *Clostridium difficile* and other multi-drug resistant organisms. Such multi-drug resistant organisms include, but shall not be limited to, MRSA, MRSE, VISA, VRSA, VRE and/or *Clostridium*.

Furthermore, and in a second aspect, the present invention provides a method of treating a subject suffering from an infection contributed to or caused by gram-positive bacteria as hereinbefore described, said method comprising the step of administering an effective amount of a therapeutically active imidazole, and derivatives thereof, and separately, simultaneously or sequentially administering an agent active on a bacterial cell surface selected from the group consisting of one or more of colistin, nisin, D-cycloserine, fosfomycin, and polymixin B, and derivatives thereof.

The method according to this aspect of the invention may comprise the administration of a therapeutically effective amount of an imidazole and a therapeutically effective amount of an agent active on a bacterial cell wall. However, it will be understood by the person skilled in the art that, due to the synergy which forms an aspect of the present invention, lesser amounts than is conventionally known to be therapeutically effective may be contemplated.

The method of the invention particularly provides a method of treating a subject suffering from an infection contributed to or caused by one or more of MRSA, MRSE, VISA, VRSA, VRE and *Clostridia* spp.

In particular, the present invention concerns the use of a compound comprising imidazole as hereinbefore described, and derivatives thereof, in combination with an agent active on a bacterial cell surface selected from the group consisting of one or more of colistin, nisin, D-cycloserine, fosfomycin, fosfomycin trometamol and polymixin B, and derivatives thereof, for the manufacture of a medicament for the treatment of infections contributed to or caused by gram-positive bacteria, such as, MRSA, MRSE, VISA, VRSA, VRE and/or *Clostridia* spp.

In addition, we provide the use of a therapeutically active imidazole, and derivatives thereof, in the manufacture of a combination medicament for treating an infection, e.g. an infection contributed to or caused by MRSA thereby reducing the emergence of VISA or VRSA.

We further provide the use of one or more of colistin, nisin, D-cycloserine, fosfomycin, or polymixin B, and derivatives thereof, in the manufacture of a combination medicament including a therapeutically active imidazole, and derivatives thereof, for treating an infection e.g. an infection contributed to or caused by gram-positive bacteria, such as, MRSA, thereby reducing the emergence of VISA or VRSA.

In addition, we provide the use of a therapeutically active imidazole, and derivatives thereof, in the manufacture of a combination medicament for treating an infection, e.g. an infection contributed to or caused by *Clostridium* spp. that inhibits both the growing bacterial cells and the vegetative spores, thereby minimising the likelihood of a relapse in infection.

We further provide a combination therapy comprising an agent capable of preventing the outgrowth of *Clostridial* spores and an agent capable of inhibiting bacterial cell growth and bacterial spore outgrowth. According to this aspect of the invention the agent capable of preventing the outgrowth of *Clostridial* spores may be one or more of colistin, nisin, D-cycloserine, fosfomycin, fosfomycin trometamol, fosfomycin disodium and polymixin B, and derivatives thereof. An agent capable of inhibiting bacterial cell growth and bacterial spore outgrowth may be an imidazole as hereinbefore described, and derivatives thereof.

We especially provide a combination therapy according to this aspect of the invention for treating an infection e.g. an infection contributed to or caused by *Clostridium* spp. thereby minimising the likelihood of a relapse in infection.

We further provide the use of an agent capable of preventing the outgrowth of *Clostridial* spores in the manufacture of a combination medicament with a therapeutically active imidazole to inhibit bacterial cell growth and bacterial spore outgrowth for treating an infection e.g. an infection contributed to or caused by *Clostridium* spp. thereby minimising the likelihood of a relapse in infection.

By way of example only, the present invention provides a synergistic combination comprising miconazole, and derivatives thereof, and fosfomycin, and derivatives thereof, which may be administered intravenously for the treatment of an infection caused by a multi-drug resistant Gram positive organism (e.g. MRSA).

In a preferred example, according to this aspect of the invention intravenous administration of the synergistic combination of miconazole and fosfomycin as hereinbefore described may be administered to a patient with an infection contributed to or caused by a multi-drug resistant Gram positive organism (e.g. MRSA, MRSE, VRE, VISA or VRSA) such that serum concentrations of miconazole and fosfomycin reach a minimum concentration of 2 mg/L and 5 mg/L respectively. The exact daily doses required to achieve these effective concentrations will depend upon, inter alia, the particular formulation used.

Thus, in a preferred example, an intravenous administration of 200 to 3600 mg/day of miconazole, and derivatives thereof, (which may be divided into 3 doses) with an amount of fosfomycin, and derivatives thereof, sufficient to be effective in providing synergy is suggested for the treatment of multi-drug resistant bacterial infections in adults. A suggested dose for intravenous administration of fosfomycin is 100 to 5000 mg tds as fosfomycin disodium. For children (1 yr-12 yrs) 20 to 40 mg/kg/day (max, 15 mg/kg/dose) miconazole with an effective (synergistic) amount of fosfomycin administered intravenously, is suggested. It will be understood that the composition for intravenous administration may comprise derivatives of miconazole and fosfomycin as hereinbefore described, but the dosage calculation hereinbefore defined shall be based upon miconazole and fosfomycin respectively.

For the treatment of infections contributed to or caused by the multi-drug resistant Gram positive organisms of the *Clostridium* genus, we particularly provide a synergistic combination comprising miconazole, and derivatives thereof, and nisin, and derivatives thereof, which may optionally be administered orally for the treatment of the infection. Thus, in a preferred example, the synergistic combination of miconazole, and derivatives thereof, with nisin, and derivatives thereof, which may be administered orally to treat an infection caused by *C. difficile*. An advantage of this synergistic combination is, inter alia, the activity of the combination of drugs on both the actively growing *C. difficile* cells and its spores. This novel approach reduces the likelihood of patient relapse, because inhibition of the bacterial spores will prevent regrowth of the organism.

A suitable dose for the treatment of *Clostridium* infections determined as gut lumen concentrations is from 0.12 to 64 mg/L of miconazole and from 0.12 to 50 mg/L nisin.

The exact daily doses to achieve such concentrations will depend upon, inter alia, the nature of the delivery device.

Devices for the delivery of such a concentration to the gut lumen include but are not limited to the following:

1. Colon-specific delivery comprising pectin beads crosslinked with zinc or any divalent, trivalent, or polycationic cation of interest, in which the beads can optionally be coated with a polycationic polymer, and/or coated with any suitable polymer for delivery to the desired part of the gastrointestinal tract such as Eudragit®-type polymers.

2. Sustained delivery systems may be used, provided they at least get past the stomach without adversely affecting the active agent(s). For example, the active agents can be admixed with a polymer that degrades or dissolves over time, releasing the active agent. These types of systems are often coated with an enteric coating, to get past the stomach, and release agents throughout the gastrointestinal tract.

3. Colon-specific delivery may be obtained by formulating the active agent with specific polymers that degrade in the colon, such as pectin. The pectin is crosslinked with a cation such as a zinc cation. The formulation, typically in the form of ionically crosslinked pectin beads, can be further coated with a suitable polymer, such as polylysine, chitin, or polyethylene imine, and/or coated with a specific polymer, such as a Eudragit® polymer.

The drug delivery systems may be formulated in accordance with the teachings of, for example, U.S. patent application Ser. No. 10/524,318, U.S. Patent Application Ser. No. 60/651,352, and International Patent application No. WO 2009/037264.

In a preferred embodiment, miconazole and nisin in an oral formulation comprising an enteric coating and designed to specifically degrade in the colon are used to deliver an effective amount of drug to inhibit both growing *C. difficile* and its vegetative spores.

By way of a second example, clotrimazole, and derivatives thereof, may be administered orally in combination with nisin to treat infections caused or contributed to by *C. difficile*. Clotrimazole is well absorbed in humans following oral administration and is eliminated mainly as inactive metabolites. Oral administration of 1.5-3-g doses of clotrimazole gave a half-life of around 3 hours; single or twice daily oral administration formulated as a synergistic combination with an agent active on a bacterial cell surface, selected from the group consisting of one or more of colistin, nisin, D-cycloserine, fosfomycin, fosfomycin trometamol or polymixin B, or a derivative or a metabolite thereof may be suitable for the treatment of multiresistant Gram positive infections with clotrimazole. A suitable combination of 1.5 to 3 g of clotrimazole with an effective concentration of nisin is contemplated for the oral treatment of multi-drug resistant gram positive infections, such as *Clostridia* spp, especially *C. difficile*.

Advantageously, synergistic combinations comprising imidazole, or derivatives thereof, with an agent active on a bacterial cell surface, selected from the group consisting of one or more of colistin, nisin, D-cycloserine, fosfomycin or polymixin B, or a derivative thereof, may be administered orally, topically to the site of an infection, transmucosally, transdermally or intravenously. Accordingly, synergistic combinations comprising an imidazole, and derivatives thereof, with an agent active on a bacterial cell surface, selected from the group consisting of one or more of one or more of colistin, nisin, D-cycloserine, fosfomycin or polymixin B, and derivatives thereof, may be formulated as polymeric nanoparticles such as alginate or polylactide-co-glycolide nanoparticles, or as sterile pharmaceutical compositions comprising a pharmaceutically acceptable carrier or excipient. Such carriers or excipients are well known to one of skill in the art and may include, for example, water, saline, phosphate buffered saline, dextrose, glycerol, ethanol, ion exchangers, alumina, aluminium stearate, lecithin, serum proteins, such as serum albumin, buffer substances such as phosphates, glycine, sorbic acid, potassium sorbate, partial glyceride mixtures of saturated vegetable fatty acids, lactic acid, water salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cyclodextrins, such as α-cyclodextrin, β-cyclodextrin, sulfobutylether$_7$-βcyclodextrin and hydroxypropyl-β-cyclodextrin, cellulose-based substances, polyethylene glycol, sodium carboxymethylcellulose, polyacrylates, waxes, polyethylene-polypropylene-block polymers, polyethylene glycol and wool fat and the like, and combinations thereof.

Synergistic combinations comprising imidazole, or derivatives thereof, with an agent active on a bacterial cell surface selected from the group consisting of colistin, nisin, D-cycloserine, fosfomycin or polymixin B, or derivatives thereof, may be administered in combination with another treatment. For example, synergistic combinations comprising an imidazole, and derivatives thereof, with an agent active on a bacterial cell surface selected from the group consisting of colistin, nisin, D-cycloserine, fosfomycin or polymixin B, and derivatives or a metabolite thereof, may be administered in combination with a chemotherapeutic agent, a detergent to facilitate, e.g. permeation, an immunostimulatory compound or drug, an oligonucleotide, a cytokine, hormone and the like.

It may be possible to administer synergistic combinations comprising an imidazole, and derivatives thereof, with an agent active on a bacterial cell surface, selected from the group consisting of one or more of colistin, nisin, D-cycloserine, fosfomycin or polymixin B, and derivatives thereof, or any combined regime as described above, transdermally via, for example, a form of transdermal delivery device. Such devices are advantageous, particularly for the administration of antibiotic compounds, as they may allow a prolonged period of treatment relative to, for example, an oral or intravenous medicament.

Examples of transdermal delivery devices may include, for example, a patch, dressing, bandage or plaster adapted to release a compound or substance through the skin of a patient. A person of skill in the art would be familiar with the materials and techniques which may be used to transdermally deliver a compound or substance and exemplary transdermal delivery devices are provided by GB2185187, U.S. Pat. No. 3,249,109, U.S. Pat. No. 3,598,122, U.S. Pat. No. 4,144,317, U.S. Pat. No. 4,262,003 and U.S. Pat. No. 4,307,717.

By way of example, synergistic combinations comprising an imidazole, and derivatives thereof, with an agent active on a bacterial cell surface, selected from the group consisting of one or more of colistin, nisin, D-cycloserine, fosfomycin or polymixin B, and derivatives thereof, may be combined with some form of matrix or substrate, such as a non-aqueous polymeric carrier, to render it suitable for use in a transdermal delivery system. This mixture may be further strengthened by the use of a woven, knitted, non-woven, or relatively open mesh fabric, to produce a patch, bandage, plaster or the like which may be temporarily attached to a particular region of a patient's body. In this way, while in contact with a patient's skin, the transdermal delivery device may release the compound or substance directly to the site of infection or through the skin of the patient as required.

The compounds provided herein may also be used as sterilising or cleaning aids for use, for example, on surfaces to reduce and/or eliminate contamination by MRSA, MRSE, VISA, VRSA, VRE and/or *Clostridia*. By way of example, synergistic combinations comprising an imidazole, and derivatives thereof, with an agent active on a bacterial cell surface selected from the group consisting of colistin, nisin, D-cycloserine, fosfomycin or polymixin B, and derivatives thereof, may be administered in combination such as, for example, a combination of miconazole or miconazole nitrate and nisin, may be prepared for application to any surface suspected of being contaminated by MRSA, MRSE, VISA, VRSA, VRE and/or *Clostridia*. For example, compounds of the present invention may be added to or diluted in an appropriate excipient or solution prior to use as a sterilising or cleaning agent. Exemplary excipients are described above. Such sterilising or cleaning solutions may be used to decontaminate, for example, furniture, floors, equipment including for example specialised hospital equipment and/or surgical equipment.

Advantageously, synergistic combinations comprising an imidazole, and derivatives thereof, with an agent active on a bacterial cell surface, selected from the group consisting of colistin, nisin, D-cycloserine, fosfomycin or polymixin B, and derivatives thereof, may be administered to a medical or veterinary surface to inhibit the growth of MRSA, MRSE, VISA, VRSA, VRE and *Clostridia*, and reduce the likelihood of the emergence and spread of, e.g. vancomycin resistance in that environment. The term "surface" used herein, refers to any surface whether medical or industrial, that provides an interface between a fluid and a solid. The interface between fluid and solid may be intermittent, and may be caused by flowing or stagnant fluid, aerosols, or other means for airborne fluid exposure. The surface described herein, refers more specifically to a plane whose mechanical structure is compatible with the adherence of bacteria such as *S. aureus* and *Enterococcus* species. In the context of the current patent, the terminology "medical or veterinary surface" encompasses the inner and outer aspects of various instruments and devices, both disposable and non-disposable. Examples include the entire spectrum of medical devices.

As used herein, the terminology "surfaces found in medical environments" includes the inner and outer aspects of various instruments and devices, whether disposable or intended for repeated uses. Examples include the entire spectrum of articles adapted for medical use, including scalpels, needles, scissors and other devices used in invasive surgical, therapeutic or diagnostic procedures; implantable medical devices, including artificial blood vessels, catheters and other devices for the removal or delivery of fluids to patients, artificial hearts, artificial kidneys, orthopaedic pins, plates and implants; catheters and other tubes (including urological and biliary tubes, endotracheal tubes, peripherally insertable central venous catheters, dialysis catheters, long term tunnelled central venous catheters, peripheral venous catheters, short term central venous catheters, arterial catheters, pulmonary catheters, Swan-Ganz catheters, urinary catheters, peritoneal catheters), urinary devices (including long term urinary devices, tissue bonding urinary devices, artificial urinary sphincters, urinary dilators), shunts (including ventricular or arterio-venous shunts); prostheses (including breast implants, penile prostheses, vascular grafting prostheses, heart valves, artificial joints, artificial larynxes, otological implants), vascular catheter ports, wound drain tubes, hydrocephalus shunts, pacemakers and implantable defibrillators, and the like. Other examples will be readily apparent to practitioners in these arts. Surfaces found in the medical environment also include the inner and outer aspects of pieces of medical equipment, medical gear worn or carried by personnel in the health care setting. Such surfaces can include counter tops and fixtures in areas used for medical procedures or for preparing medical apparatus, tubes and canisters used in respiratory treatments, including the administration of oxygen, of solubilised drugs in nebulisers and of aesthetic agents. Also included are those surfaces intended as biological barriers to infectious organisms in medical settings, such as gloves, aprons and face-shields. Commonly used materials for biological barriers may be latex-based or non-latex based, such as vinyl. Other such surfaces can include handles and cables for medical or dental equipment not intended to be sterile. Additionally, such surfaces can include those non-sterile external surfaces of tubes and other apparatus found in areas where blood or body fluids or other hazardous biomaterials are commonly encountered.

In a further embodiment, the compounds described herein may be used to eliminate and/or reduce contamination by MRSA, MRSE, VISA, VRSA, VRE and *Clostridia* on parts of the body, particularly for example, the hands. Synergistic combinations comprising an imidazole, and derivatives thereof, with an agent active on a bacterial cell surface, selected from the group consisting of one or more of colistin, nisin, D-cycloserine, fosfomycin or polymixin B, and derivatives thereof, may be diluted as an aqueous or non-aqueous solution (dissolved in aqueous, non aqueous or organic solvent) and which may be applied to a body part, for example, the hands. Such a solution may find particular application in, for example, hospitals, care homes and or nurseries where the prevalence and transmission rates of MRSA, MRSE, VISA, VRSA, VRE and *Clostridia* are often high.

In a further embodiment, the methods and medicaments described herein may be used prophylactically as a means to prevent the development of an infection caused or contributed to by MRSA, MRSE, VISA, VRSA, VRE and *Clostridia*, or to reduce the likelihood of the development of VISA or VRSA, e.g. from an MRSA infection. Medicaments and/or methods for prophylactic use may be administered or applied to any person or mammal at risk of developing an infection caused or contributed to by MRSA, MRSE, VISA, VRSA, VRE and *Clostridia*. For example, people working in care homes, nursing homes, sports centres, community centres, shops, restaurants, cafes, nurseries and/or schools may require prophylactic treatments.

Thus, the invention provides the composition as hereinbefore described for prophylactic use.

Advantageously, the medicaments and/or methods described herein may have particular application in institutions housing, sheltering, caring or otherwise holding people or patients vulnerable to or "at risk" of developing or contracting MRSA, MRSE, VISA, VRSA, VRE and *Clostridia*. The medicaments and methods may be particularly useful in hospitals, nursing homes, nurseries and/or schools. More generally, an elderly, young or immunocompromised person or patient may particularly benefit from the medicaments and methods described herein. Moreover, the methods and medicaments of the present invention may be particularly useful to those undergoing a prolonged stay in hospital, for example in an intensive care facility.

Additionally, or alternatively, the medicaments and methods described herein may be useful in community centres, sports facilities, shops, restaurants, cafes or other places where transmission of bacteria, particularly MRSA, MRSE, VISA, VRSA, VRE and *Clostridia*, is likely.

Thus, the invention also provides the composition as hereinbefore described for use in a sterilization and/or cleaning aid.

Referring to the examples and figures that follow, it is understood that the invention is not limited to the embodiments set forth herein for illustration, but embraces all such forms thereof as come within the scope of the above disclosure.

DETAILED DESCRIPTION

Figure 1:
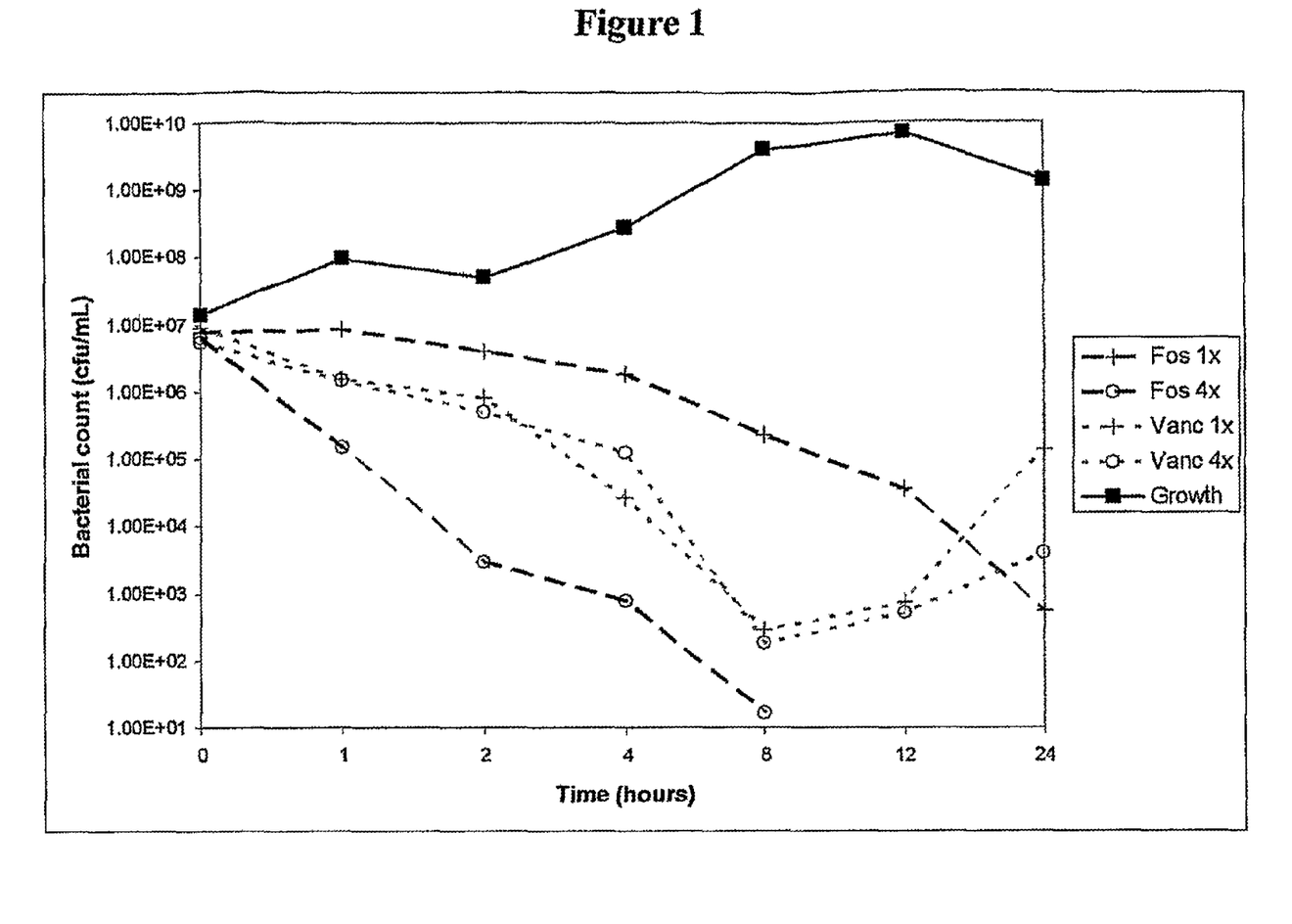
FIG. 1 shows the kill curves achieved for an MRSA strain in the presence of miconazole and fosfomycin at 4× the MIC (black dashed line with circle markers) vs the current standard treatment vancomycin at 4× the MIC (grey dotted line with circle markers).
Figure 2:
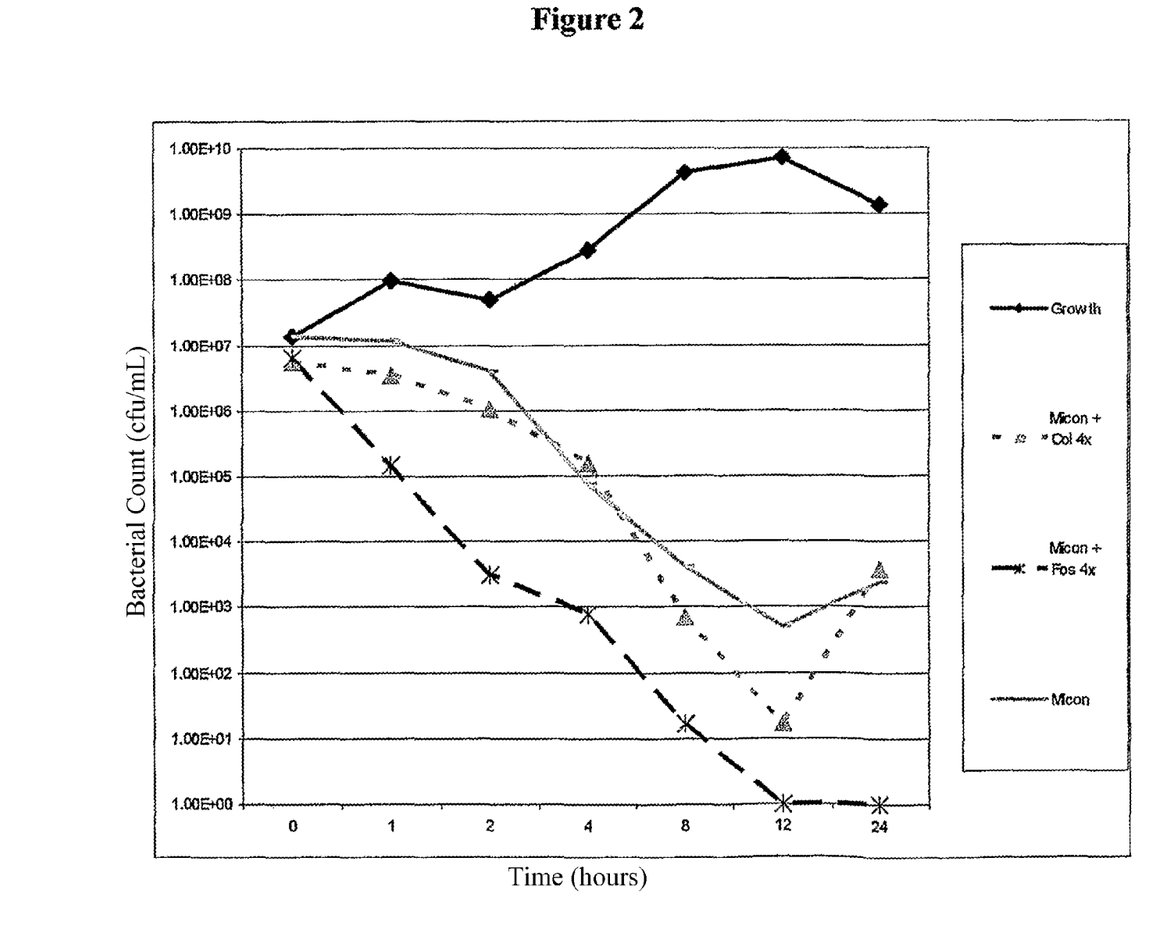
FIG. 2, shows the kill curves obtained when MRSA is challenged with miconazole used singly (grey line) compared with miconazole in combination with a sub-inhibitory concentration of fosfomycin (Micon+fos 4×, black dashed line), and miconazole in combination with a sub-inhibitory concentration of colistin (Micon+Col 4×, grey dotted line), demonstrating clear synergy of the combinations of miconazole with colistin and miconazole with fosfomycin.
Figure 3:
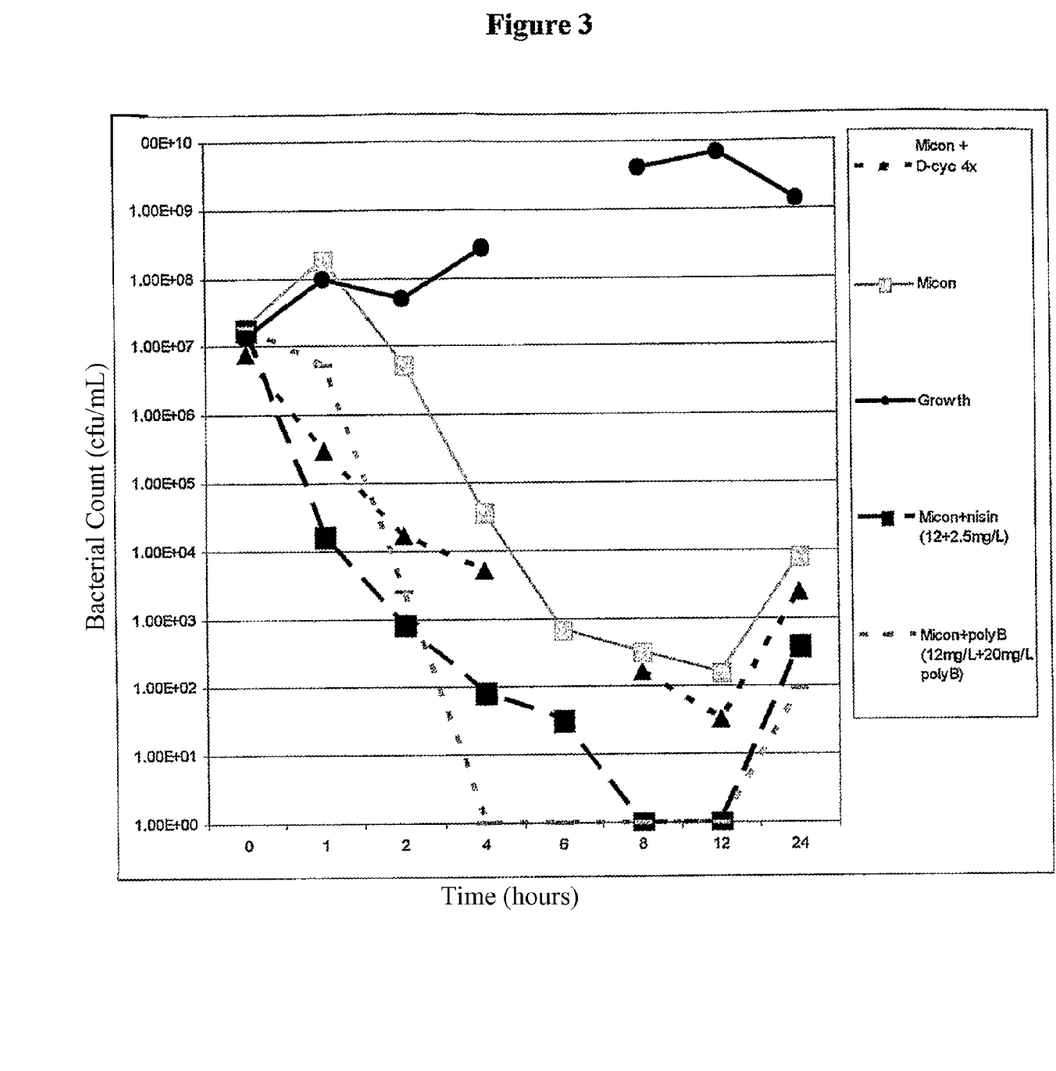
FIG. 3, shows the kill curves obtained when MRSA is challenged with miconazole used singly (Grey line, square markers) compared with miconazole in combination with a sub-inhibitory concentration of D-cycloserine (Micon+D-cyc 4×, black dashed line, triangle markers), miconazole in combination with a sub-inhibitory concentration of nisin (Miconazole+nisin 4×, black dashed line, square markers), and miconazole in combination with a sub-inhibitory concentration of polymixin B (Miconazole+polymixin B, Grey dotted line), demonstrating clear synergy of the combinations of miconazole with D-cycloserine, miconazole with nisin, and miconazole with polymixin B.

Methods:

In example experiments miconazole nitrate, econazole nitrate and clotrimazole were dissolved in DMSO. Colistin, D-cycloserine, fosfomycin and polymixin B were dissolved in water. Nisin was suspended at 10 mg/mL in 0.02 M HCl, and the supernatant fraction following centrifugation at 10,000 g for 10 mins was used in the following experiments.

Other solvents that may be used include caster oil, pyridine, and 0.9% saline. For IV administration agents may be solubilised in polyethoxylated caster oil, or cyclodextrins such as sulfobutylether$_7$-βcyclodextrin or hydroxypropyl-β-cyclodextrin and lactic acid. Minimum inhibitory concentrations (MICs) of a range of clinical and control bacterial organisms were measured according to BSAC (British Society for Antimicrobial Chemotherapy) guidelines (Andrews 2001), for single agents. The method of determining MICs of imidazole with colistin, D-cycloserine, fosfomycin, polymixin B, or nisin is described briefly as follows. MICs were measured by agar dilution. Kill curves were performed in accordance with the methods of Garrison and Nuemiller, 2007. Briefly kill profiles were generated by logarithmically plotting mean CFU/mL data over time. Total logarithmic reductions in bacterial counts were determined by subtracting 24 h CFU/mL values from starting inocula.

Preparation of Agar Plates and Broths.

Stock solutions of each agent were prepared using the formula:

$$\frac{1000}{P} \times V \times C = W$$

Where

P=μg of active compound per mg (μg/mg)

V=volume required (mL)

C=final concentration of solution (mg/L)

W=weight of agent (mg) to be dissolved in volume V (mL)

Stock solutions were prepared at concentrations of 1000 mg/L and 100 mg/L. To determine the MIC of miconazole, the appropriate amount of each stock solution were added to separate Petri dishes give a range of final concentrations (after the addition of 20 mL molten agar): from 0.12 to 32 mg/L. To determine the MICs of miconazole with the specific agent active on a bacterial cell surface, these concentrations of miconazole were used in addition to a fixed sub-inhibitory amount of the agent active on a bacterial cell surface. The amounts of cell membrane or cell wall active agents used were as follows: colistin, 5 mg/L; D-cycloserine, 10 mg/L; fosfomycin, 5 mg/L; polymixin B, 20 mg/L; nisin, 2.5 mg/L. These concentrations were demonstrated to have no inhibitory effect on the growth of the bacterial strains tested, hence any decrease in the MIC of miconazole observed in the presence of these cell-surface active agents indicates synergy. Volumes (20 mL) of cooled molten IST agar (oxoid) was added to each Petri dish and mixed by swirling. After drying, the plates were stored at 4° C. and protected from light. Plates were used on the day of preparation.

Preparation of Inoculum

The test organisms were grown overnight in 5 mL IST broth. Using a dilution in 0.9% saline of 1:100, the appropriate agar plates were inoculated using a multipoint inoculator.

Incubation

Agar plates and microtitre plates were incubated at 37° C. in air for 18-20 hours.

Interpretation of Results

The MIC is the minimum amount of an antibiotic at which there is no visible growth of bacteria. Tiny single colonies or faint hazes were not counted as growth. Synergy was reported if the inhibitory effect of the drugs in combination were greater than the sum of the inhibitory effects of each drug singly. The concentration of miconazole, with or without the cell membrane or cell wall active agent, capable of inhibiting the growth of 50% and 90% of the strains tested is reported as the $MIC_{50}$ and $MIC_{90}$ respectively. The range of MICs for each group of bacterial strains is also reported.

Results:

Tables 1a, b, c, d, and e, show the $MIC_{50}$, $MIC_{90}$ and range for each combination tested. For each of these combinations, a decrease in the MICs for the combination compared to miconazole used singly, demonstrates a synergistic effect.

TABLE 1a $MIC_{50}$, $MIC_{90}$ and range for cycloserine, used at 10 mg/L in combination with miconazole. MRSA AND VRE (n = 27 and 5 respectively)

| Drug | MIC 50 | MIC 90 | Range |
|---|---|---|---|
| Miconazole | 2 | 2 | 0.5-8 |
| D-cycloserine 10 mg/L | 1 | 2 | <0.25-8 |

TABLE 1b $MIC_{50}$, $MIC_{90}$ and range for fosfomycin, used at 5 mg/L in combination with miconazole. MRSA AND VRE (n = 27 and 5 respectively)

| Drug | MIC 50 | MIC 90 | Range |
|---|---|---|---|
| Miconazole | 2 | 2 | 0.5-8 |
| Fosfomycin 5 mg/L | 1 | 2 | <0.25-8 |

TABLE 1c $MIC_{50}$, $MIC_{90}$ and range for colistin, used at 5 mg/L in combination with miconazole. MRSA AND VRE (n = 21 and 3 respectively)

| Drug | MIC 50 | MIC 90 | Range |
|---|---|---|---|
| Miconazole | 2 | 4 | 1-6 |
| Colistin 5 mg/L | 1 | 2 | 0.25-6 |

TABLE 1d $MIC_{50}$, $MIC_{90}$ and range for polymixin B, used at 20 mg/L in combination with miconazole. MRSA AND VRE (n = 21 and 3 respectively)

| Drug | MIC 50 | MIC 90 | Range |
|---|---|---|---|
| Miconazole | 2 | 4 | 1-6 |
| Polymixin B 20 mg/L | 1 | 2 | 0.25-6 |

TABLE 1e $MIC_{50}$, $MIC_{90}$ and range for nisin B, used at 2.5 mg/L in combination with miconazole. MRSA AND VRE (n = 21 and 4 respectively)

| Drug | MIC 50 | MIC 90 | Range |
|---|---|---|---|
| Miconazole | 2 | 4 | 0.5-8 |
| Nisin 2.5 mg/L | 2 | 2 | <0.25-2 |

TABLE 2

MICs of other imidazoles demonstrating a lack of activity with bifonazole ketoconazole and fluconazole.

| Bacteria | Strain | Bifonazole | Ketoconazole | Fluconazole |
|---|---|---|---|---|
| VISA | VISA 3900 UK | >128 | 64 | >128 |
| VISA | USA/VISA 5827 | >128 | 64 | >128 |
| Enterococcus faecium (VRE) | NCTC 7171 | >128 | 128 | >128 |
| Staphylococcus epidermidis | ATCC 1228 | >128 | 64 | >128 |
| VISA | USA/VISA 5836 | >128 | 64 | >128 |

TABLE 2-continued

MICs of other imidazoles demonstrating a lack of activity with bifonazole ketoconazole and fluconazole.

| Bacteria | Strain | Bifonazole | Ketoconazole | Fluconazole |
|---|---|---|---|---|
| Enterococcus faecium (VRE) | E19 UAA/522 VanB | >128 | 128 | >128 |
| Enterococcus faecalis (VRE) | E8 VanA | >128 | >256 | >128 |
| Enterococcus faecium (VRE) | VanR B145344C LFE | >128 | 128 | >128 |
| Enterococcus faecium (VRE) | E15 VanA ATCC 4147 | >128 | 16 | >128 |
| Escherichia coli | NCTC 10418 | >128 | >256 | >128 |
| Pseudomonas aeruginosa | NCTC 10662 | >128 | >256 | >128 |

TABLE 3

MICs of miconazole, with and without bacitracin demonstrating a lack of synergy with this combination against multi-drug resistant strains. Here a 1:1 ratio bacitracin to miconazole was used in one experiment, and a fixed sub-inihibitory concentration of bacitracin (2.5 mg/L) in the second experiment.
MRSA AND VRE (n = 27 and 5 respectively)

| Drug | MIC 50 | MIC 90 | Range |
|---|---|---|---|
| Miconazole | 2 | 2 | 0.5-8 |
| Bacitracin:miconazole 1:1 | 4 | 4 | 2-8 |
| Bacitracin 2.5 mg/L | 2 | 2 | 0.5-4 |

This data shows no synergy between bacitracin and miconazole, and no benefit of the addition of 2.5 mg/L bacitracin to miconazole in decreasing the miconazole MIC.

Table 4, below, shows the synergy observed by the combination of miconazole with nisin, vs these agents used singly.

TABLE 4

| Strain | Miconazole | Nisin | Miconazole + 2.5 mg/L nisin |
|---|---|---|---|
| E. faecium ATCC 7171 | 0.5 | 4 | <0.25 |
| E1 E. gall ATCC 12359 VanC | 1 | 4 | <0.25 |
| E. faecium VanR B145344C LFE | 4 | 8 | <0.25 |
| E15 VanAATCC4147 E. faecium | 2 | 4 | <0.25 |
| PF 99b 983237K BERIAN CLONE | 2 | 8 | 2 |
| PF 116a 981695K | 2 | 8 | 2 |
| PF 15a 009521M ST22 EMRSA | 1 | 8 | 2 |
| PF 16a 00923R EMRSA 16 | 2 | 4 | 1 |
| PF 153a 026225E | 0.5 | 8 | 2 |
| S113 MRSA | 2 | 4 | <0.25 |
| LF10 | 2 | 8 | 2 |
| LF11 | 2 | 4 | 1 |
| LF12 | 2 | 4 | 1 |
| LF13 | 2 | 8 | 2 |
| LF14 | 2 | 8 | 2 |
| LF15 | 2 | 8 | 2 |
| LF16 | 2 | 4 | 2 |
| LF17 | 2 | 4 | <0.25 |
| LF18 | 1 | 4 | <0.25 |
| LF19 | 2 | 8 | 2 |
| USA/VISA 5827 | 2 | >20 | 1 |
| Mu3ex Japan | 2 | >20 | 1 |
| Mu50ex Japan | 1 | >8 | 0.5 |
| USA/VISA 5836 | 4 | >8 | 2 |
| VISA 3900 UK | 2 | >20 | 1 |

Table 5, below, shows the inhibitory effect of the synergistic combination of miconazole and nisin against various clinicial isolates of *Clostridium difficile*.

TABLE 5

| Strain | Miconazole | Micon + 0.5 mg/L nisin |
|---|---|---|
| 83 | >16 | <0.25 |
| 28 | >16 | <0.25 |
| 58 | >16 | <0.25 |
| 41 | >16 | <0.25 |
| 97 | >16 | <0.25 |
| 130 | >16 | <0.25 |
| 184 | >16 | <0.25 |
| 23 | >16 | <0.25 |
| 87 | >16 | <0.25 |
| 84 | >16 | <0.25 |
| 99A | >16 | <0.25 |
| 57 | >16 | <0.25 |
| 185 | >16 | <0.25 |
| 47 | >16 | <0.25 |
| 31 | >16 | <0.25 |
| 30 | >16 | <0.25 |
| 98A | >16 | <0.25 |
| 77 | >16 | <0.25 |
| 126 | >16 | <0.25 |
| 102 | >16 | <0.25 |
| 96 | >16 | <0.25 |
| 120 | >16 | <0.25 |
| 5 | >16 | <0.25 |
| 169 | >16 | <0.25 |
| 186 | >16 | <0.25 |

The invention claimed is:

1. A method of treating a subject suffering from an infection contributed to or caused by multi-drug resistant Gram positive organisms of the *Clostridium* genus, said method comprising the step of administering an effective amount of miconazole, and pharmaceutically acceptable salts thereof, and nisin, and pharmaceutically acceptable salts thereof, separately, simultaneously or sequentially.

2. A method according to claim 1 wherein the multi-drug resistant Gram positive organisms of the *Clostridium* genus are *C. difficile*.

3. A method according to claim 1 wherein administering comprises oral administration.

4. A method according to claim 1 wherein administering comprises intravenous administration.

* * * * *